(12) United States Patent
Yamada et al.

(10) Patent No.: US 9,380,786 B2
(45) Date of Patent: Jul. 5, 2016

(54) AGENT FOR PREVENTING BACTERIAL WILT DISEASE, AND METHOD FOR PREVENTING BACTERIAL WILT DISEASE

(75) Inventors: Takashi Yamada, Hiroshima (JP); Makoto Fujie, Hiroshima (JP); Takeru Kawasaki, Hiroshima (JP)

(73) Assignee: Hiroshima University, Hiroshima (JP)

( * ) Notice: Subject to any disclaimer, the term of this patent is extended or adjusted under 35 U.S.C. 154(b) by 0 days.

(21) Appl. No.: 14/113,802

(22) PCT Filed: Apr. 27, 2012

(86) PCT No.: PCT/JP2012/061399
§ 371 (c)(1),
(2), (4) Date: Oct. 24, 2013

(87) PCT Pub. No.: WO2012/147928
PCT Pub. Date: Nov. 1, 2012

(65) Prior Publication Data
US 2014/0044679 A1 Feb. 13, 2014

(30) Foreign Application Priority Data
Apr. 28, 2011 (JP) .................. 2011-102153

(51) Int. Cl.
| A61K 49/00 | (2006.01) |
| A61K 48/00 | (2006.01) |
| A61K 39/108 | (2006.01) |
| A01N 63/00 | (2006.01) |
| C12N 1/20 | (2006.01) |
| C12N 7/00 | (2006.01) |

(52) U.S. Cl.
CPC *A01N 63/00* (2013.01); *C12N 1/20* (2013.01); *C12N 7/00* (2013.01); *C12N 2795/14121* (2013.01); *C12N 2795/14131* (2013.01)

(58) Field of Classification Search
CPC ....... A61K 39/02; A61K 48/00; A61K 49/00; A01N 63/00
USPC ............. 424/9.1, 9.2, 93.1, 93.2, 93.4, 93.47, 424/93.6, 260.1
See application file for complete search history.

(56) References Cited

FOREIGN PATENT DOCUMENTS

| JP | 63-022005 | 1/1988 |
| JP | 2005-278513 | 10/2005 |
| JP | 2007-252351 | 10/2007 |
| JP | 2011-041527 | 3/2011 |

OTHER PUBLICATIONS

Askora, A., et al. Virology, vol. 384, pp. 69-76, 2009.*
Askora el al., "Phase engineering II: design for new host range of Ralstonia solanacearum phage RSM." Abstracts of the Annual Meeting of the Society for Biotechnology. Japan, 2007, vol. 60, p. 116.
Askora el al., "Host Recognition and integration of filamentous phage •RSM in the phytopathogen, Ralstonia solanacearum." Virology 384 (2009) 69-76.
Askora et al., "Resolvase-like serine recombinase mediates integration/excision in the bacteriophage •RSM." J. Biosci. Bioeng. 2011, vol. 111, No. 2, p. 109-116.
Kawasaki et al., "Genomic Characterization of Filamentous Integrative Bacteriophages, •RSS1 and •RSM1, Which Infect Ralstonia Solanacearum." J. Bacteriol vol. 189, No. 16, 2007, 5792-5802.
Satsuma et al., "Diagnostic utilization of RSS1 and RSM1, bacteriophages infecting Ralstonia solanacearum." Abstracts of the Annual Meeting of the Society of Biotechnology, Japan, 2008, vol. 60, p. 116.
Yamada et al., "New bacteriophages that infect the phytopathogen Ralstonia solanacearum," Microbiology, 2007, 153-2630-2639.
Office Action From Chinese Patent Office Dated Aug. 25, 2014. Original Chinese and English Translation.
Guo Jianhua et al. "Mechanism and method for biocontrol of plant bacterial wilt diseases," Chinese Journal of Biological Control, 13:42-43, 1997. English Translation.
Labrie SJ et al. "Bacteriophage resistance mechanisms," Nature Reviews Microbiology 8:317-327, 2010.
Office Action From Japanese Patent Office Dated May 12, 2015 for Japanese Application No. 2011-102153, Original Japanese and English Translation enclosed.
Askora, A. et al., Host recognition and integration of filamentous phage ϕ RSM in the phytopathogen, Ralstonia solanace, Virology, vol. 384, No. 1. pp. 69-76 (2009).
Ogawa, K. et al., Biological control of Fusarium wilt of sweet potato by use of non-pathogenic Fusarium oxysporum, The Phytopathological Society of Japan Bulletin, vol. 50, No. 1, pp. 1-9 (1984), Abstract-translation Only.
Amemiya, Y. et al., Suppression of Fusarium wilt of tomato by use of the cross protection, Chiba University Faculty of Horticulture Technical Bulletin, vol. 37, pp. 79-83 (1986), Abstract Translation Only.
Katsube, K. et al.Control of Fusarium wilt of spinach by use of non-pathogenic Fusarium oxysporum, The Phytopathological Society of Japan Bulletin, vol. 63, No. 5, pp. 389-394 (1997), Abstract Translation Only.

* cited by examiner

*Primary Examiner* — Rodney P Swartz
(74) *Attorney, Agent, or Firm* — K&L Gates, LLP; Louis Cullman; Michelle Glasky Bergman

(57) ABSTRACT

Provided are: an agent for preventing bacterial wilt disease, which agent can prevent the development of bacterial wilt disease caused by various different bacterial wilt disease strains, that is, the development of bacterial wilt disease in various different plant varieties; and a method for preventing bacterial wilt disease utilizing the agent for preventing bacterial wilt disease. The agent for preventing bacterial wilt disease comprises as an active ingredient a wilt bacterium (*Ralstonia solanacearum*) infected with the ϕRSM1-type filamentous phage and/or the ϕRSM3-type filamentous phage. The method for preventing bacterial wilt disease comprises the step of inoculating the agent for preventing bacterial wilt disease to a plant. The plant is preferably any one of tomato, potato, green pepper, eggplant, tobacco, capsicum, Japanese basil, Japanese radish, strawberry, banana, marguerite, chrysanthemum and sunflower.

10 Claims, 9 Drawing Sheets

FIG.1

| BACTERIAL WILT DISEASE STRAIN | φRSM1 | φRSM3 | φRSS1 |
|---|---|---|---|
| C319 | − | + | + |
| M4S | + | − | − |
| Ps29 | + | − | − |
| Ps65 | + | − | − |
| Ps72 | − | + | − |
| Ps74 | + | + | − |
| MAFF106603 | − | + | + |
| MAFF106611 | − | + | + |
| MAFF211270 | + | + | − |
| MAFF211271 | − | + | − |
| MAFF211272 | − | + | − |
| MAFF301556 | − | + | − |
| MAFF301558 | − | + | − |
| MAFF730138 | + | − | − |
| MAFF730139 | − | + | + |

FIG.2

| BACTERIAL WILT DISEASE STRAIN | RACE | BIOVAR | PHYLOTYPE | HOST PLANT |
|---|---|---|---|---|
| C319 | 1 | ND[a] | I | TOBACCO |
| M4S | 1 | 3 | I | TOBACCO |
| Ps29 | 1 | 3 | I | TOBACCO |
| Ps65 | 1 | ND | I | TOBACCO |
| Ps72 | 1 | ND | I | TOBACCO |
| Ps74 | 1 | ND | I | TOBACCO |
| MAFF106603 | 1 | 3 | I | TOMATO |
| MAFF106611 | 1 | 4 | I | EGGPLANT |
| MAFF211270 | 1 | N2 | I | TOMATO |
| MAFF211271 | 1 | N2 | IV | POTATO |
| MAFF211272 | 3 | 4 | I | CURCUMA |
| MAFF301556 | 4 | 4 | I | POTATO |
| MAFF301558 | 1 | N2 | IV | POTATO |
| MAFF730138 | 1 | 3 | I | TOMATO |
| MAFF730139 | 1 | 4 | I | EGGPLANT | a: NOT DETERMINED.

| PROPERTY | ΦRSM3-UNINFECTED | ΦRSM3-INFECTED |
|---|---|---|
| COLONY SHAPE | ADHESIVE | LESS ADHESIVE |
| COLONY SIZE | LARGE | SMALL |
| COLOR OF CULTURE LIQUID | WHITE/YELLOW | YELLOW/BROWN |
| COLONY EDGE | MM: IRREGULAR | MM: ROUND |
| TWITCHING MOTILITY | MM: HIGH | MM: LOW OR ABSENT |
| AGGREGATION FORMATION | LOW PROBABILITY | HIGH PROBABILITY |
| SENSITIVITY TO ANTIBIOTICS | CONTENT IN PLATE | CONTENT IN PLATE |
| CHLORAMPHENICOL | $<20\,\mu g/ml$ | $>40\,\mu g/ml$ |
| AMPICILLIN | $<40\,\mu g/ml$ | $<40\,\mu g/ml$ |
| KANAMYCIN | $<30\,\mu g/ml$ | $>60\,\mu g/ml$ |

AGENT FOR PREVENTING BACTERIAL WILT DISEASE, AND METHOD FOR PREVENTING BACTERIAL WILT DISEASE

CROSS REFERENCE TO RELATED APPLICATIONS

The present application is a 371 of International Application No. PCT/JP2012/061399 filed on Apr. 27, 2012, which claims the benefit to Japanese Patent Application Serial No. 2011-102153 filed on Apr. 28, 2011, the contents of both of which are hereby incorporated by reference in their entirety.

TECHNICAL FIELD

The present invention relates to an agent for preventing bacterial wilt disease that uses a wilt bacterium (*Ralstonia solanacearum*) infected with a bacteriophage, and a method for preventing bacterial wilt disease using the agent for preventing bacterial wilt disease.

BACKGROUND ART

Bacterial wilt disease (damping-off) is a disease infectious to not less than 200 species of plants including solanaceous plants, and causes death of the plants, leading to serious damage to agriculture. In cases where progression of the disease occurs rapidly, the plant dies while the plant remains green, and it is said that the name was given because of such a fact. The disease has a characteristic that, when the stem of a plant suffering from bacterial wilt disease is cut at a position near the soil and immersed in water, milky mucus (bacterial ooze) exudes from the stem.

As main pesticides for bacterial wilt disease, chloropicrin and methyl bromide have been proposed. However, both chloropicrin and methyl bromide are dangerous drugs. Furthermore, methyl bromide is an ozone depleting substance, and use of methyl bromide has been banned since 2005. In general, bacterial wilt disease occurs in relatively warm regions, but the trend of global warming has accelerated spreading of the wilt bacterium and a decline in production of crops thereby, already causing loss of about 9.5 trillion yens per year in the world.

As described above, bacterial wilt disease occurs in relatively warm regions. However, wilt of potato caused by a cold-adapted bacterial wilt disease strain, race 3 biovar 2 phylotype II has already become a major threat to the United States, and it is said that spreading of the strain to Japan is just a matter of time. Thus, alternative means for effectively preventing or controlling the wilt bacterium are being developed and studied in Japan and other countries.

For example, Patent Literature 1 describes a method for controlling soil-borne diseases in solanaceous plants. More specifically, the literature describes a method wherein living bacteria of the *Pseudomonas solanacearum* (current academic name, *Ralstonia solanacearum*; which corresponds to the wilt bacterium) strain M4S; and a bacteriophage that causes bacteriolysis of both of the bacterium and pathogenic *Pseudomonas solanacearum*; are immobilized, and the obtained immobilized substance is applied to the soil. Patent Literature 2 describes a method for controlling the wilt bacterium by spraying a bacteriophage itself that causes bacteriolysis of the wilt bacterium onto the plant or the soil. The literature also describes a method for improving soil by addition of the bacteriophage to the soil.

On the other hand, Patent Literature 3, and Non Patent Literature 1 and Non Patent Literature 3 describe details of bacteriophages that specifically infect the wilt bacterium. For example, the ϕRSM1-type filamentous phage, ϕRSM3-type filamentous phage and ϕRSS1-type filamentous phage, which do not cause bacteriolysis of the wilt bacterium, are described in detail.

CITATION LIST

Patent Literature

Patent Literature 1: Unexamined Japanese Patent Application Kokai Publication No. S63-22005, Jan. 29, 1988.
Patent Literature 2: Unexamined Japanese Patent Application Kokai Publication No. 2005-278513, Oct. 13, 2005
Patent Literature 3: Unexamined Japanese Patent Application Kokai Publication No. 2011-041527, Mar. 3, 2011.

Non Patent Literature

Non Patent Literature 1: Takashi Yamada, Takeru Kawasaki, Shoko Nagata, Akiko Fujiwara, Shoji Usami and Makoto Fujie, 2007, New bacteriophages that infect the phytopathogen *Ralstonia solanacearum*, Microbology 153, 2630-2639
Non Patent Literature 2: Takeru Kawasaki, Shoko Nagata, Akiko Fujiwara, Hideki Satsuma, Makoto Fujie, Shoji Usami, and Takashi Yamada, 2007, Genomic Characterization of Filamentous Integrative Bacteriophages, ϕRSS1 and ϕRSM1, That Infect *Ralstonia solanacearum*, J. Bacteriol 189, 5792-5802
Non Patent Literature 3: Askora A., Kwasaki T., Usami S., Fujie M., and Yamada T., 2009, Host recognition and integration of filamentous phage ϕRSM in the phytopathogen, *Ralstonia solanacearum*, Virology 384, 69-76

SUMMARY OF INVENTION

Technical Problem

However, as described above, the problem of bacterial wilt disease has recently become more serious. Therefore, various vaccine-like substances (substances that reduce, by injection of a weak pathogen in advance to induce production of antibodies, the risk of development of infectious diseases caused thereafter by similar pathogens) are required in order to enable prevention, control and the like of development of bacterial wilt diseases caused by various bacterial wilt disease strains of different races (strains isolated from different hosts, or having different host ranges), biovars (strains of different physiological types, or having different capacities of acid production) and phylotypes (strains of different bacterial groups).

The present invention was made in view of the above-described circumstances, and aims to provide an agent for preventing bacterial wilt disease that can prevent development of bacterial wilt disease caused by various different bacterial wilt disease strains, that is, development of bacterial wilt disease in various different plant varieties; and a method for preventing bacterial wilt disease using the agent for preventing bacterial wilt disease.

Solution to Problem

As a result of intensive study to achieve the above-described purposes, the present inventors discovered that a wilt bacterium infected with the ϕRSM1-type filamentous phage (*Ralstonia* phage RSM1; DDBJ accession number AB259123) (hereinafter referred to as the φRSM1 phage) or the φRSM3-type filamentous phage (*Ralstonia* phage RSM3, DDBJ accession number AB434711) (hereinafter referred to as the φRSM3 phage) loses the pathogenicity, and that inoculation of the bacterium to a plant such as tomato does not cause development of bacterial wilt disease. Further, the present inventors discovered that, in cases where a wilt bacterium infected with the phage is preliminarily inoculated to a plant such as tomato, the plant shows strong resistance to a wilt bacterium having strong pathogenicity inoculated thereafter and does not develop bacterial wilt disease for at least 2 months. An application for deposition of the φRSM1 phage in the state where a wilt bacterium is infected with the phage was submitted to Patent Microorganisms Depositary, National Institute of Technology and Evaluation (2-5-8 Kazusakamatari, Kisarazu-shi, Chiba 292-0818 Japan) as of Apr. 19, 2011, and the phage was deposited under the microorganism identification reference φRSM1/M4S and the accession No. NITE P-1085, which was followed by request for conversion to deposition under the Budapest Treaty and then acceptance under the accession No. NITE BP-1085. Further, an application for deposition of the φRSM3 phage in the state where a wilt bacterium is infected with the phage was submitted to Patent Microorganisms Depositary, National Institute of Technology and Evaluation (2-5-8 Kazusakamatari, Kisarazu-shi, Chiba 292-0818 Japan) as of Apr. 19, 2011, and the phage was deposited under the microorganism identification reference φRSM3/106603 and the accession No. NITE P-1086, which was followed by request for conversion to deposition under the Budapest Treaty and then acceptance under the accession No. NITE BP-1086.

Figure 1:
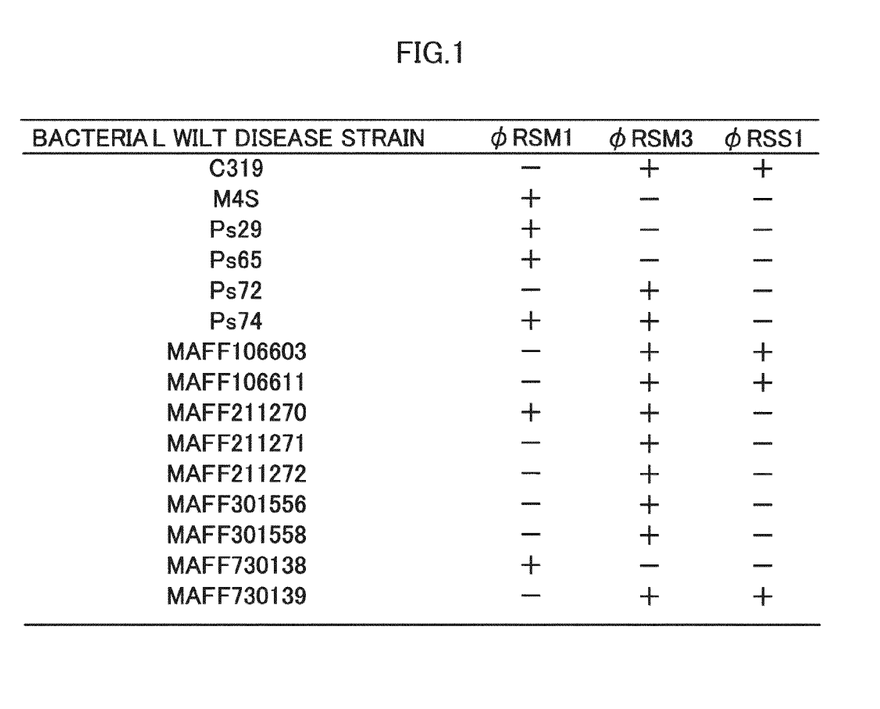
FIG. 1 is a diagram showing the host specificities of the φRSM-type filamentous phages of the present invention.
Figure 2:
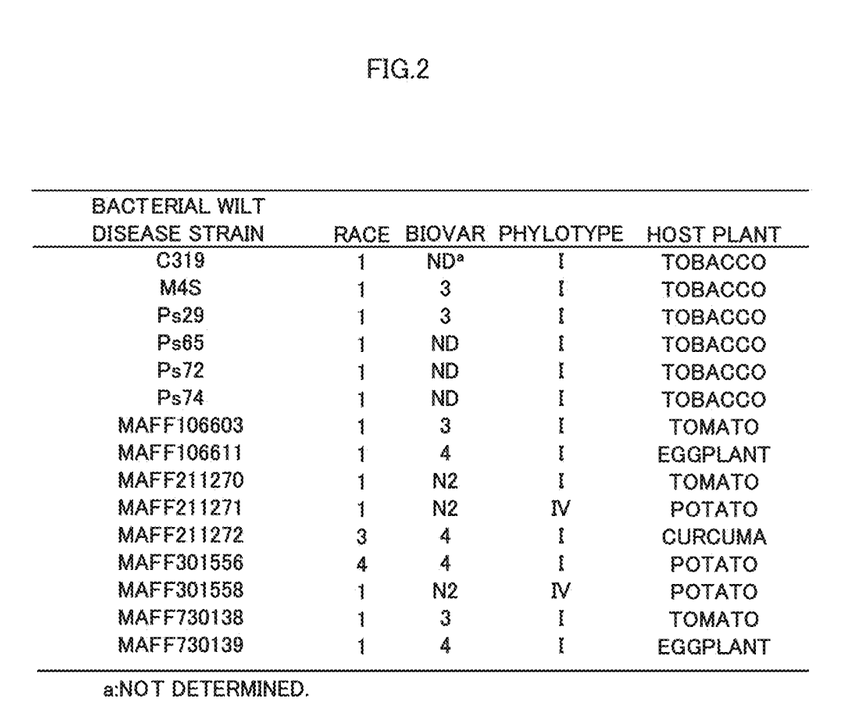
FIG. 2 is a diagram showing properties of various bacterial wilt disease strains.

Further, the host specificity to bacterial wilt disease strains is largely different between the φRSM1 phage and the φRSM3 phage. It was therefore discovered that use of the two phages allows prevention of development of the bacterial wilt diseases caused by a total of 15 bacterial wilt disease strains of different races, biovars and phylotypes. Accordingly, it was expected that various naturally occurring bacterial wilt disease strains are likely to be infected with either the φRSM1 phage or the φRSM3 phage. FIG. 1 is a diagram showing the host specificities of the φRSM-type filamentous phages. In FIG. 1, + represents sensitivity to each bacterial strain, and – represents insensitivity. The φRSS1 phage (*Ralstonia* phage RSS1; DDBJ accession number, AB259124) is a control. Similarly to the φRSM1 and φRSM3 phages, the φRSS1 phage uses wilt bacteria as hosts, and does not cause bacteriolysis (see Non Patent Literature 2). As shown in FIG. 1, unlike the combination of the φRSM1 phage and the φRSM3 phage having a wide range of sensitivity, the φRSS1 phage failed to infect many bacterial wilt disease strains. FIG. 2 is a diagram showing properties of various bacterial wilt disease strains. For the details shown in FIG. 2, see "Mitsuo Horita and Kenichi Tsuchiya, 2002, Microorganism Genetic Resources Manual (12)—Wilt Bacterium *Ralstonia solanacearum*—, National Institute of Agrobiological Sciences".

Thus, the agent for preventing bacterial wilt disease of the first mode of the present invention comprises as an effective component a wilt bacterium (*Ralstonia solanacearum*) infected with the φRSM1-type filamentous phage and/or the φRSM3-type filamentous phage.

The wilt bacterium (*Ralstonia solanacearum*) strain infected with the φRSM1-type filamentous phage is preferably any one of M4S, Ps29, Ps65 and Ps74.

The wilt bacterium (*Ralstonia solanacearum*) strain infected with the φRSM3-type filamentous phage is more preferably any one of C319, Ps72 and Ps74.

The method for preventing bacterial wilt disease of the second mode of the present invention comprises the step of inoculating the agent for preventing bacterial wilt disease of the first mode to a plant.

The plant is preferably any one of tomato, potato, green pepper, eggplant, tobacco, capsicum, Japanese basil, Japanese radish, strawberry, banana, marguerite, chrysanthemum and sunflower.

The plant is more preferably any one of tomato, potato, green pepper, eggplant and tobacco.

The method for preventing bacterial wilt disease preferably comprises inoculating the wilt bacterium (*Ralstonia solanacearum*) in an amount of $10^5$ to $10^8$ cells/g plant body weight.

The method for preventing bacterial wilt disease more preferably comprises inoculating the wilt bacterium (*Ralstonia solanacearum*) in an amount of $10^6$ to $10^7$ cells/g plant body weight.

The agent for preventing bacterial wilt disease is preferably inoculated to the stem of the plant.

The agent for preventing bacterial wilt disease is more preferably inoculated to the stem of the plant at a site 1 to 4 cm distant from the soil.

The agent for preventing bacterial wilt disease is still more preferably inoculated 2 to 4 weeks after germination of the plant.

Advantageous Effects of Invention

By the present invention, an agent for preventing bacterial wilt disease, which agent can prevent the development of bacterial wilt disease caused by various different bacterial wilt disease strains, that is, the development of bacterial wilt disease in various different plant varieties; and a method for preventing bacterial wilt disease using the agent for preventing bacterial wilt disease; are provided.

DESCRIPTION OF EMBODIMENTS

Modes of the present invention are described below in detail. In the present description, the terms such as "have", "include" and "comprise" also include the meanings of "consist of" and "be constituted by".

(Agent for Preventing Bacterial Wilt Disease)

The first mode of the present invention relates to an agent for preventing bacterial wilt disease, comprising as an effective component a wilt bacterium infected with the φRSM1 phage and/or the φRSM3 phage. The φRSM1 phage has a DNA base sequence homology of not less than 90% to the φRSM3 phage, and the major difference between the phages is the structure of the host recognition protein pIII. Phages and prophages having high homologies to such phages (φRSM1 phage and φRSM3 phage) can be found in the genome databases such as the above-described DDBJ and NCBI (National Center for Biotechnology Information). Therefore, the phages and prophages having genome sequence homologies of not less than 90% to such phages are suggested to have properties of the same lineage. For details of other properties of the φRSM1 phage and the φRSM3 phage, see Patent Literature 3, and Non Patent Literature 1 and Non Patent Literature 3, as described above.

As described above, in the present description, the term "bacterial wilt disease (damping-off)" means a disease that is infectious to not less than 200 species of plants including solanaceous plants and causes death of the plants, leading to serious damage to agriculture. Accordingly, in the present description, the "agent for preventing bacterial wilt disease" is not limited as long as the agent is a vaccine-like composition that enables prevention or inhibition of symptoms, disease damages and the like of, or that delays development of, bacterial wilt disease. Further, the agent for preventing bacterial wilt disease of the first mode of the present invention may comprise other substances, compositions and the like that are pharmaceutically and botanically acceptable, in addition to the wilt bacterium infected with a phage as an effective component.

The method of infection of the wilt bacterium with the φRSM1 phage or the φRSM3 phage may be any method known to those skilled in the art. For example, the method may be a method in which the φRSM1 phage or the φRSM3 phage separated, purified and grown from a bacterial wilt disease strain infected with the lysogenic type of each phage is added to a culture liquid of a wilt bacterium prepared by culturing in CPG liquid medium, followed by culturing and growing the phage, wherein an appropriate bacterial wilt disease strain is selected by reference to FIG. 1 and FIG. 2 (see Non Patent Literature 1 or Non Patent Literature 3). Examples of the lysogenic type of the φRSM1 phage include the bacterial wilt disease strains MAFF211270, Ps29 and Ps74, and examples of the lysogenic type of the φRSM3 phage include MAFF 106611, MAFF211272 and MAFF730139.

The "agent for preventing bacterial wilt disease comprising as an effective component a wilt bacterium infected with (either one of) the φRSM1 phage and the φRSM3 phage" in the first mode of the present invention is described in detail. In the case of an agent for preventing bacterial wilt disease comprising as an effective component a wilt bacterium infected with the φRSM1 phage, the bacterial wilt disease strain is not limited as long as the strain is a bacterial wilt disease strain that can be infected with the φRSM1 phage. Further, in the case of an agent for preventing bacterial wilt disease comprising as an effective component a wilt bacterium infected with the φRSM3 phage, the bacterial wilt disease strain is not limited as long as the strain is a bacterial wilt disease strain that can be infected with the φRSM3 phage. For the bacterial wilt disease strains that can be infected with each phage, see FIG. 1 and "Mitsuo Horita and Kenichi Tsuchiya, 2002, Microorganism Genetic Resources Manual (12)—Wilt Bacterium *Ralstonia solanacearum*—, National Institute of Agrobiological Sciences".

More specifically, examples of the bacterial wilt disease strains that can be infected with the φRSM1 phage include M4S, Ps29, Ps65, Ps74, MAFF211270 and MAFF730138. On the other hand, examples of the bacterial wilt disease strains that can be infected with the φRSM3 phage include C319, Ps72, Ps74, MAFF 106603, MAFF106611, MAFF211270, MAFF211271, MAFF211272, MAFF301556, MAFF301558 and MAFF730139.

As can be seen from FIG. 1, use of these two phages allows infection of a total of 15 bacterial wilt disease strains of different races, biovars and phylotypes. The bacterial wilt disease strains of different races, biovars and phylotypes here cause development of bacterial wilt disease in various different plant varieties. That is, by using agents for preventing bacterial wilt disease of the first mode of the present invention (phage vaccine) prepared using these two phages in an appropriate combination, it is possible to prevent development of bacterial wilt disease caused by various different bacterial wilt disease strains, that is, to prevent development of bacterial wilt disease in various different plant varieties.

In terms of the "agent for preventing bacterial wilt disease comprising as an effective component a wilt bacterium infected with (both of) the φRSM1 phage and the φRSM3 phage" in the first mode of the present invention, since, for example, MAFF211270 has host specificities to both phages as shown in FIG. 1, an agent for preventing bacterial wilt disease comprising as an effective component a wilt bacterium infected with both φRSM1 phage and φRSM3 phage is also possible. Further, an agent for preventing bacterial wilt disease comprising as effective components a plurality of types of bacterial wilt disease strains is also possible.

Figure 3:
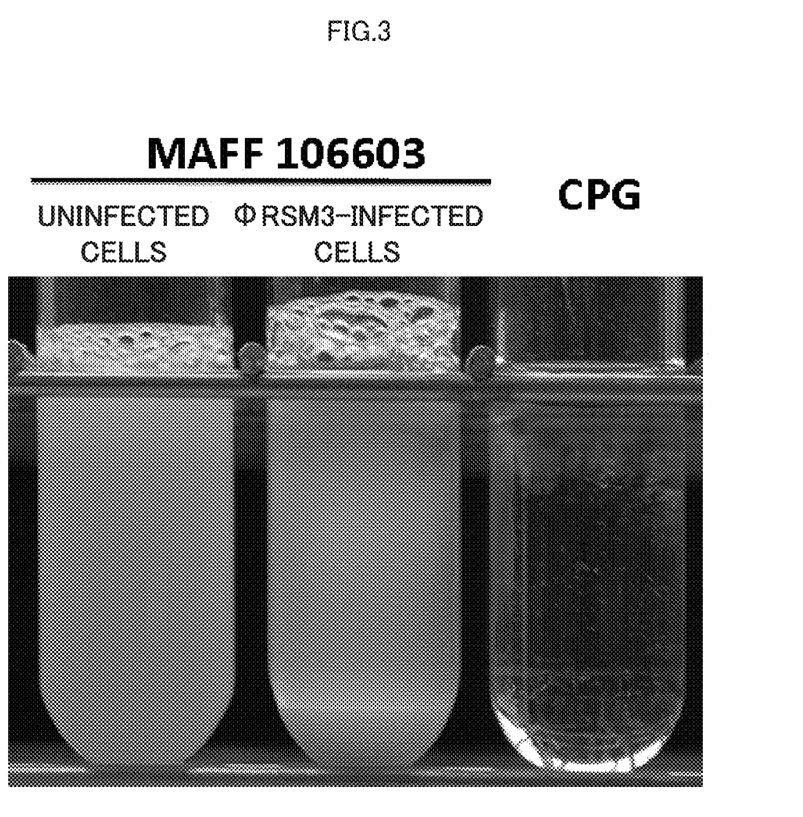
FIG. 3 is a diagram showing the appearance of the bacterial wilt disease strain MAFF106603 infected with the φRSM3 phage, after culturing in CPG liquid medium.

The difference between the phage-infected bacterial wilt disease strain and the phage-uninfected bacterial wilt disease strain is described below in detail by way of specific examples. FIG. 3 is a diagram showing the appearance of the φRSM3 phage-infected bacterial wilt disease strain MAFF106603 after culturing in CPG liquid medium. In FIG. 3, culture liquid of the φRSM3 phage-uninfected bacterial wilt disease strain MAFF 106603 is shown in the left (Uninfected cells), and culture liquid of the φRSM3 phage-infected bacterial wilt disease strain MAFF106603 is shown in the middle (φRSM3-infected cells). Both were obtained by culturing the cells in CPG liquid medium with shaking in the late logarithmic growth phase, followed by being left to stand for 2 hours. The appearance of CPG liquid medium that does not contain the wilt bacterium is shown in the right (CPG). As shown in FIG. 3, precipitation easily occurs in the culture liquid of the φRSM3 phage-infected bacterial wilt disease strain MAFF106603, while the culture liquid of the φRSM3 phage-uninfected bacterial wilt disease strain MAFF106603 is still in the suspended state.

Figure 4:
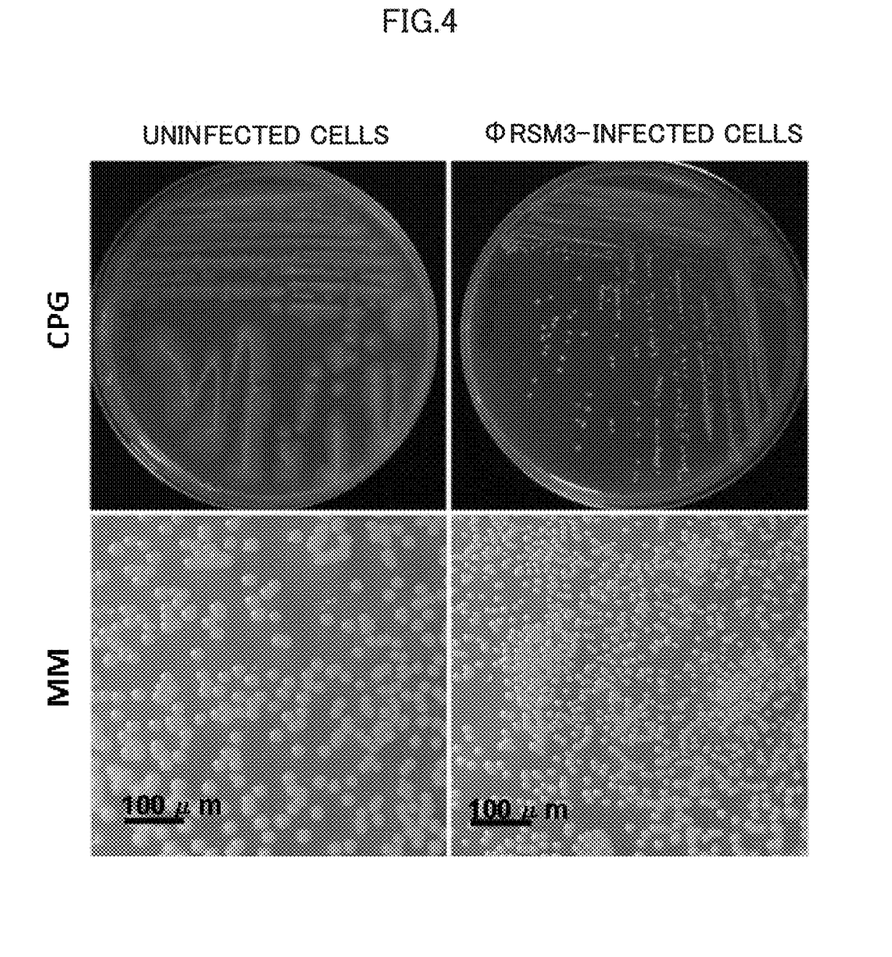
FIG. 4 is a diagram showing the morphology of colonies of the bacterial wilt disease strain MAFF106603 infected with the φRSM3 phage, MM indicates minimal medium.

FIG. 4 is a diagram showing the morphology of colonies of φRSM3 phage-infected bacterial wilt disease strain MAFF106603. In FIG. 4, the upper left panel (Uninfected cells, CPG)) shows colonies of the φRSM3 phage-uninfected bacterial wilt disease strain MAFF106603 on a CPG plate; the upper right panel (φRSM3-infected cells, CPG)) shows colonies of the φRSM3 phage-infected bacterial wilt disease strain MAFF106603 on a CPG plate; the lower left panel (Uninfected cells, MM) shows colonies of the φRSM3 phage-uninfected bacterial wilt disease strain MAFF106603 on an MM (minimal medium) plate; and the lower right panel (φRSM3-infected cells, MM) shows colonies of the φRSM3 phage-infected bacterial wilt disease strain MAFF106603 on an MM plate. As shown in FIG. 4, the colonies on the CPG plate of the φRSM3 phage-uninfected bacterial wilt disease strain MAFF106603 have rough edges and irregular shapes. However, the colonies on the CPG plate of the φRSM3 phage-infected bacterial wilt disease strain MAFF106603 are smaller than the colonies of the φRSM3 phage-uninfected bacterial wilt disease strain MAFF106603, and have round shapes. Also on the MM plates, the colonies of the φRSM3 phage-infected bacterial wilt disease strain MAFF106603 are much smaller than the colonies of the φRSM3 phage-uninfected bacterial wilt disease strain MAFF106603.

Figure 5:
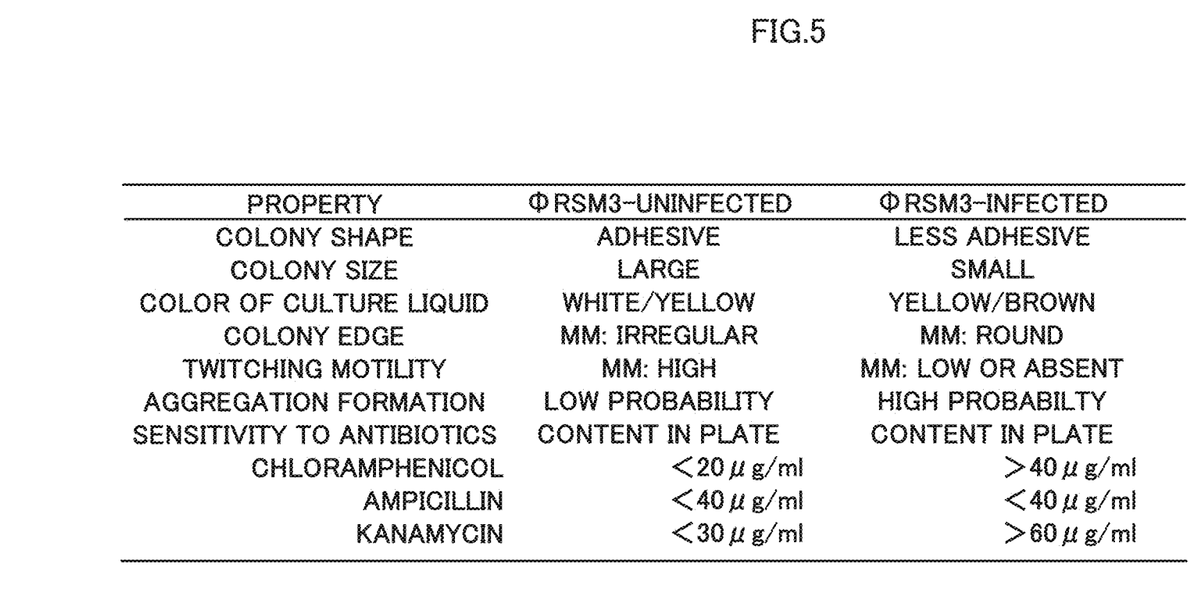
FIG. 5 is a diagram showing detailed properties of the bacterial wilt disease strain MAFF106603 infected with the φRSM3 phage, and the bacterial wilt disease strain MAFF106603 that is not infected therewith.
Figure 6:
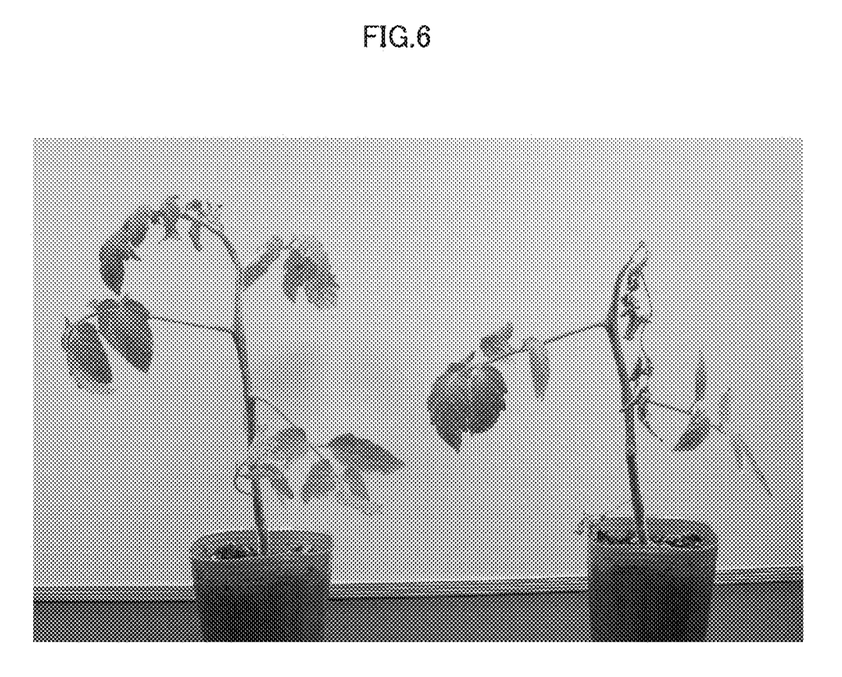
FIG. 6 is a diagram showing the result of an experiment for confirming the pathogenicity of the φRSM3 phage-infected bacterial wilt disease strain MAFF106603 of Example 1. In cases where $10^6$ to $10^7$ cells are inoculated to tomato seedlings at a site between the second and third true leaves above the ground on Week 1 to Week 6 after germination, the φRSM3 phage-infected bacterial wilt disease strain MAFF106603 does not affect the growth of the tomato plants after the inoculation (left). However, the uninfected bacterial wilt disease strain MAFF106603 completely killed the part upper than the site of inoculation by Day 4 to Week 1 (right). These results were 100% reproducible in 5 replicates for each condition.

Thus, infection of the bacterial wilt disease strain MAFF106603 with the φRSM3 phage remarkably changes the morphology and characteristics of the bacterial wilt disease strain MAFF106603. FIG. 5 is a diagram showing detailed properties of the φRSM3 phage-infected bacterial wilt disease strain MAFF106603 and uninfected bacterial wilt disease strain MAFF106603.

(Method for Preventing Bacterial Wilt Disease)

The second mode of the present invention relates to a method for preventing bacterial wilt disease, which method comprises inoculating the agent for preventing bacterial wilt disease comprising as an effective component a wilt bacterium (*Ralstonia solanacearum*) infected with the φRSM1-type filamentous phage and/or the φRSM3-type filamentous phage to a plant, that is, inoculating the above-described agent for preventing bacterial wilt disease of the first mode to a plant.

In the present description, the "plant" includes all plants that are known to those skilled in the art and may develop bacterial wilt disease (damping-off). Examples of the plant include tomato, potato, green pepper, eggplant, tobacco, capsicum, Japanese basil, Japanese radish, strawberry, banana, marguerite, chrysanthemum and sunflower. The plant is preferably any one of tomato, potato, green pepper, eggplant and tobacco. In the present description, the meaning of the term "inoculation" is the same as the meaning of the term "inoculation" generally used by those skilled in the art, including injection using an injection needle to the stem of a plant or the like, and injection by attaching the agent for preventing bacterial wilt disease to the tip of a toothpick, followed by puncturing the stem therewith.

The term "inoculation of the agent for preventing bacterial wilt disease to a plant" means inoculation of the above-described agent for preventing bacterial wilt disease of the first mode to an appropriate plant variety. That is, the term means inoculation of an agent for preventing bacterial wilt disease comprising as an effective component a bacterial wilt disease strain infected with a phage whose race (host range) and the like are appropriate.

The part where the agent for preventing bacterial wilt disease is to be inoculated is preferably the stem of the plant, and the agent is inoculated more preferably to the stem of the plant at a site 1 to 4 cm distant from the soil (a site near the soil), most preferably to the stem of the plant at a site 2 to 3 cm distant from the soil. The inoculum dose of the agent for preventing bacterial wilt disease may be determined appropriately depending on the species and variety of each plant. For example, the concentration of the agent for preventing bacterial wilt disease may be adjusted such that $10^5$ to $10^8$ cells, preferably $10^6$ to $10^7$ cells, most preferably about $10^6$ cells, per gram (g) plant body weight of a wilt bacterium infected with the ϕRSM1 phage or the ϕRSM3 phage are inoculated. Further, the timing of inoculation of the agent for preventing bacterial wilt disease may be selected appropriately depending on the growth of each plant and the above-described site of inoculation. For example, the timing of inoculation is 1 to 5 weeks after germination of the plant, preferably about 2 to 4 weeks after germination.

In such a method, inoculation of the above-described agent for preventing bacterial wilt disease of the first mode to a plant allows the plant to maintain resistance to the wilt bacterium for not less than 2 months. The plant also has similar resistance to different strains of wilt bacterium having strong pathogenicity (see Example 2 (2-1, 2-2 and 2-3)).

EXAMPLES

The present invention is described below in more detail by way of Preparation Example and Examples, but the Preparation Examples and Examples do not limit the present invention. The Preparation Example and Examples below were carried out under the conditions for the method described in detail in "Mitsuo Horita and Kenichi Tsuchiya, 2002, Microorganism Genetic Resources Manual (12)—Wilt Bacterium *Ralstonia solanacearum*—, National Institute of Agrobiological Sciences".

Preparation Example

Figure 7:
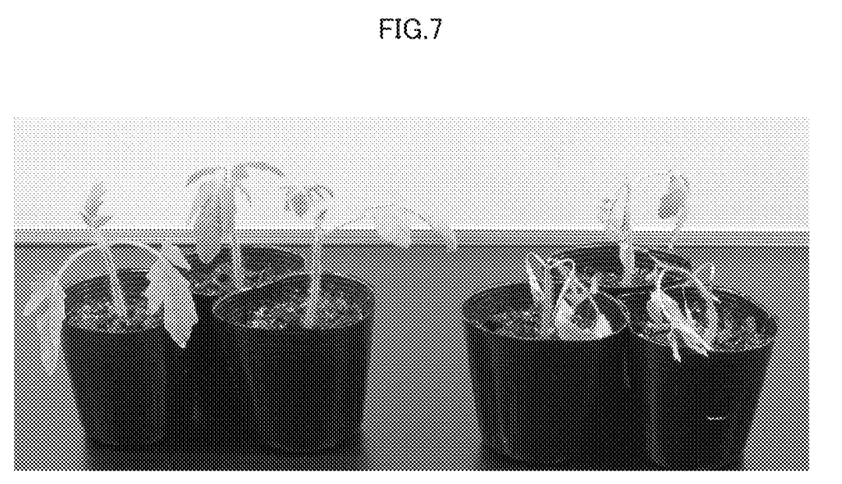
FIG. 7 is a diagram showing the result of an experiment for studying the resistance in Example 2-1 wherein treatment with the φRSM3 phage-infected bacterial wilt disease strain MAFF106603 was followed by secondary inoculation of the bacterial wilt disease strain MAFF106603 on the next day. Primary inoculation of $10^6$ to $10^7$ cells of the φRSM3 phage-infected bacterial wilt disease strain MAFF106603 or *E. coli* as a control was carried out for tomato seedlings on Day 10 after germination at a site below the first true leaf, and secondary inoculation of $10^6$ to $10^7$ cells of the bacterial wilt disease strain MAFF106603 was carried out on the next day at the site 5 mm upper than the site of primary inoculation. As a result, the tomato plants for which the primary inoculation of the φRSM3 phage-infected bacterial wilt disease strain MAFF106603 was carried out grew normally (left). However, the tomato plants for which the primary inoculation of *E. coli* as a control was carried out were completely killed by Day 4 to Week 1 (right). These results were 100% reproducible in 3 replicates for each condition.

Preparation examples for the wilt bacterium and the phages are briefly described below. Various bacterial wilt disease strains (all of which were obtained from National Institute of Agrobiological Sciences (Japan)) before infection with the phages were prepared by culturing in a CPG liquid medium comprising 0.1% casamino acid, 1% peptone and 0.5% glucose in distilled water at 28° C. with shaking at 200 to 300 rpm. In terms of the phages, the ϕRSM3 phage was grown using as a host bacterium the bacterial wilt disease strain MAFF106611, and the ϕRSM1 phage was grown using as a host bacterium the bacterial wilt disease strain M4S. More specifically, each phage was added to each host bacterium grown in CPG medium (early logarithmic growth phase, $OD_{600}$=0.1), such that MOI=0.01 to 0.05 was achieved, and the bacterium was then cultured for 16 to 18 hours, followed by removal of the bacterial cells by centrifugation (8,000×g), filtration of the obtained supernatant through a filtration membrane (0.2 μm), treatment of the resulting filtrate with 0.5 M NaCl and 5% polyethylene glycol 6000, and then collection of the precipitate by centrifugation (15,00×g, for 30 minutes at 4° C.) to prepare phage particles. These operations allow collection of the ϕRSM1 phage or the ϕRSM3 phage with an yield of $10^{12}$ PFU//ml. The phages can be stably stored at a low temperature (4° C.). For details, see Patent Literature 3, and Non Patent Literature 1 or Non Patent Literature 3.

Example 1

In the present Example 1, an experiment for confirming the pathogenicity of the ϕRSM3 phage-infected bacterial wilt disease strain MAFF106603 is described in detail.

The bacterial wilt disease strain MAFF106603 was infected with the prepared ϕRSM3 phage (MOI=10), and a single colony was selected on a CPG agar medium (pH 6.8 to 7.0) comprising 0.1% casamino acid, 1% peptone, 0.5% glucose and 1.7% agar in distilled water (confirmed by restriction enzyme treatment). The colony was cultured with shaking in a CPG liquid medium comprising 0.1% casamino acid, 1% peptone and 0.5% glucose in distilled water at 28° C. to $OD_{600}$=0.2. Thereafter, 5 μl of the culture liquid was inoculated to a site between the second and third true leaves of tomato plants (Saturn) 1 to 6 weeks after germination using a sterile syringe. As a control, the bacterial wilt disease strain MAFF106603 uninfected with the ϕRSM3 phage was inoculated to tomato plants (Saturn) under the same conditions. The inoculation treatment was carried out for 5 tomato plants in each case, and the plants were cultivated in an artificial climate chamber (28° C., with a light/dark cycle of 16:8 hours).

FIG. 6 is a diagram showing the result of an experiment for confirming the pathogenicity of the ϕRSM3 phage-infected bacterial wilt disease strain MAFF106603 of Example 1. As shown in FIG. 6, the tomato plant to which the ϕRSM3 phage-infected bacterial wilt disease strain MAFF106603 was inoculated (left) did not develop bacterial wilt disease. The other 4 tomato plants subjected to the same treatment also showed healthy growth, and did not show any symptom of bacterial wilt disease even 2 months after the inoculation (not shown). On the other hand, as shown in FIG. 6, all control tomato plants (right), to which the ϕRSM3 phage-uninfected bacterial wilt disease strain MAFF106603 was inoculated, showed symptoms of bacterial wilt disease within 4 days to 1 week after the inoculation, and the stem/leaves upper than the inoculation site died. From the results of the present Example 1, it could be confirmed that ϕRSM3 phage-infected bacterial wilt disease strain MAFF106603 does not show pathogenicity to tomato.

Example 2

In the present Example 2, an experiment for confirming the resistance of tomato plants treated with the ϕRSM3 phage-infected bacterial wilt disease strain MAFF106603 to the bacterial wilt disease strain MAFF106603 is described in detail.

First, in the same manner as in the above-described Example 1, the ϕRSM3 phage prepared was infected the bacterial wilt disease strain MAFF106603 (MOI=10), and a single colony was selected on a CPG agar medium (pH 6.8 to 7.0) comprising 0.1% casamino acid, 1% peptone, 0.5% glucose and 1.7% agar in distilled water (confirmed by restriction enzyme treatment). Subsequently, the colony was cultured with shaking in a CPG liquid medium comprising 0.1% casamino acid, 1% peptone and 0.5% glucose in distilled water at 28° C. to $OD_{600}$=0.2. Thereafter, 5 μl of the culture liquid was inoculated to the stems (at a site 2 to 3 cm distant from the soil) of tomato plants (Saturn) after 1.5 weeks after germination, using a sterile syringe. As a control, *E. coli* JM109 was inoculated to tomato plants (Saturn) under the same conditions. The inoculation treatment was carried out for 3 plants in each case, and the tomato plants (Saturn) were cultivated in an artificial climate chamber (28° C., with a light/dark cycle of 16:8 hours).

Example 2-1

The present Example 2-1 describes a case in which the 3 tomato plants (Saturn) after the above-described inoculation treatment in each case were subjected to inoculation (at a site 3 to 4 cm distant from the soil) of the ϕRSM3 phage-uninfected bacterial wilt disease strain MAFF106603 having strong pathogenicity in the same manner as described above on the next day of the above-described inoculation.

FIG. 7 is a diagram showing the result of the experiment for studying the resistance in Example 2-1 wherein treatment with the ϕRSM3 phage-infected bacterial wilt disease strain MAFF106603 was followed by secondary inoculation of the bacterial wilt disease strain MAFF106603 on the next day. As shown in FIG. 7, the inoculation (secondary inoculation) of the bacterial wilt disease strain MAFF106603 to the tomato plants to which the ϕRSM3 phage-infected bacterial wilt disease strain MAFF106603 had been inoculated did not cause development of bacterial wilt disease (left). All tomato plants to which the ϕRSM3 phage-infected bacterial wilt disease strain MAFF106603 was inoculated showed the same result, and no development of the disease was found thereafter. On the other hand, as shown in FIG. 7, all tomato plants to which the control, *E. coli* JM109, was inoculated showed symptoms of bacterial wilt disease by 2 to 3 days after the secondary inoculation, and died 4 days to 1 week later (right). From the results of the present Example 2-1, it could be confirmed that the tomato plants to which the φRSM3 phage-infected bacterial wilt disease strain MAFF106603 was inoculated show resistance to the secondary inoculation (on the next day) of the bacterial wilt disease strain MAFF106603.

Example 2-2

The present Example 2-2 describes a case in which the 3 tomato plants after the above-described inoculation treatment in each case were subjected to inoculation (at a site 4 to 5 cm distant from the soil) of the bacterial wilt disease strain MAFF106603 in the same manner as described above 2 weeks after the inoculation.

Figure 8:
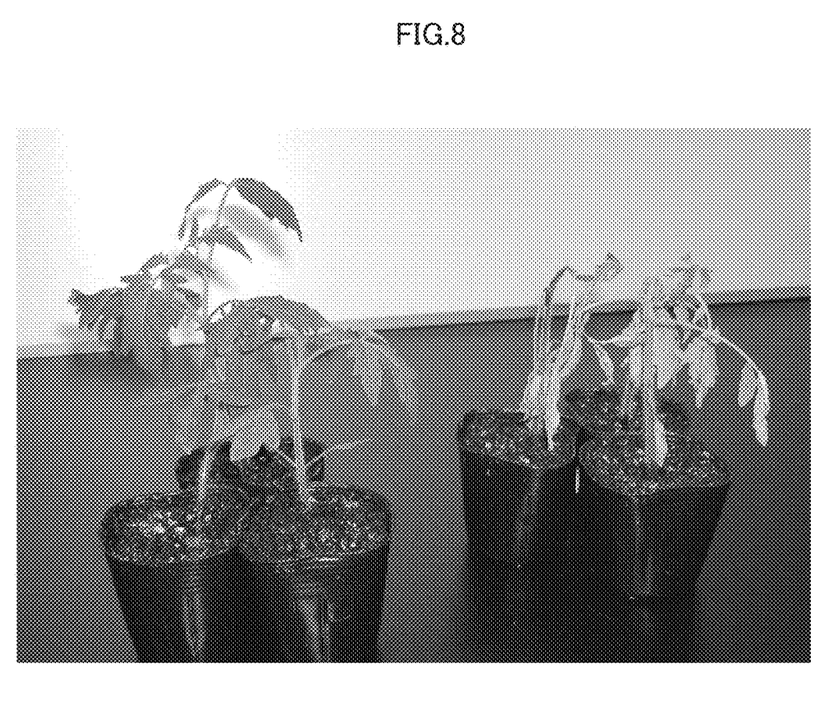
FIG. 8 is a diagram showing the result of an experiment for studying the resistance in Example 2-2 wherein treatment with the φRSM3 phage-infected bacterial wilt disease strain MAFF106603 was followed by secondary inoculation of the bacterial wilt disease strain MAFF106603 two weeks later. Primary treatment of tomato seedlings was carried out in the same manner as in Experiment Example 2-1, and secondary inoculation of $10^6$ to $10^7$ cells of the bacterial wilt disease strain MAFF106603 was carried out two weeks later. As a result, the tomato plants for which the primary inoculation of the φRSM3 phage-infected bacterial wilt disease strain MAFF106603 was carried out grew normally (left). However, the tomato plants for which the primary inoculation of *E. coli* as a control was carried out were completely killed by Day 4 to Week 1 (right). These results were 100% reproducible in 3 replicates for each condition.

FIG. 8 is a diagram showing the result of the experiment for studying the resistance in Example 2-2 wherein treatment with the φRSM3 phage-infected bacterial wilt disease strain MAFF106603 was followed by secondary inoculation of the bacterial wilt disease strain MAFF106603 two weeks later. As shown in FIG. 8, even after the secondary inoculation to the tomato plants to which the φRSM3 phage-infected bacterial wilt disease strain MAFF106603 had been inoculated, the plants were healthy, and did not develop the disease thereafter (left). On the other hand, as shown in FIG. 8, all tomato plants to which the control, *E. coli* JM109, was inoculated showed symptoms of bacterial wilt disease by 2 to 3 days after the secondary inoculation, and died 4 days to 1 week later (right). From the results of the present Example 2-2, it could be confirmed that the tomato plants to which the φRSM3 phage-infected bacterial wilt disease strain MAFF106603 was inoculated also show resistance to the secondary inoculation (two weeks later) of the bacterial wilt disease strain MAFF106603.

Example 2-3

The present Example 2-3 describes a case in which the 5 tomato plants after the above-described inoculation treatment in each case were subjected to inoculation (at a site 8 to 10 cm distant from the soil) of the bacterial wilt disease strain MAFF106603 in the same manner as described above 2 months after the inoculation.

Figure 9:
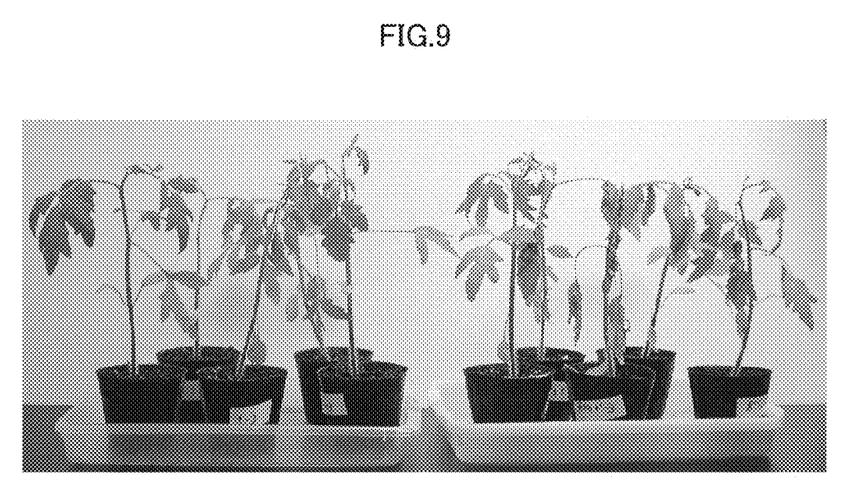
FIG. 9 is a diagram showing the result of an experiment for studying the resistance in Example 2-3 wherein treatment with the φRSM3 phage-infected bacterial wilt disease strain MAFF106603 was followed by secondary inoculation of the bacterial wilt disease strain MAFF106603 two months later. Primary treatment of tomato seedlings was carried out in the same manner as in Experiment Example 2-1, and secondary inoculation of $10^6$ to $10^7$ cells of the bacterial wilt disease strain MAFF106603 was carried out two months later. As a result, the tomato plants for which the primary inoculation of the φRSM3 phage-infected bacterial wilt disease strain MAFF106603 was carried out grew normally (left). However, the tomato plants for which the primary inoculation of *E. coli* as a control was carried out showed wilting in the part upper than the site of inoculation by Day 4 to Week 1 (right). These results were 100% reproducible in 5 replicates for each condition.

FIG. 9 is a diagram showing the result of the experiment for studying the resistance in Example 2-3 wherein treatment with the φRSM3 phage-infected bacterial wilt disease strain MAFF106603 was followed by secondary inoculation of the bacterial wilt disease strain MAFF106603 two months later. As shown in FIG. 9, even after the secondary inoculation to the tomato plants to which the φRSM3 phage-infected bacterial wilt disease strain MAFF106603 had been inoculated, the plants were healthy, and did not develop the disease thereafter (left). On the other hand, as shown in FIG. 9, all tomato plants to which the control, *E. coli* JM109, was inoculated showed symptoms of bacterial wilt disease 4 days to 1 week after the secondary inoculation (right). From the results of the present Example 2-3, it could be confirmed that the tomato plants to which the φRSM3 phage-infected bacterial wilt disease strain MAFF106603 was inoculated also show resistance to the secondary inoculation (two months later) of the bacterial wilt disease strain MAFF106603.

Further, when secondary inoculation of the bacterial wilt disease strain MAFF106603 was carried out for tomato plants treated with the φRSM1 phage-infected bacterial wilt disease strain MAFF211270 and the φRSM3 phage-infected bacterial wilt disease strain MAFF106611 using the same method and conditions as in the above-described Example 2 (2-1, 2-2 and 2-3), completely the same result on the resistance could be confirmed (not shown). The result indicates that the effect on the resistance to the secondary inoculation is the same even in cases where a different combination of phage-infected bacterial wilt disease strains was inoculated. Thus, it is suggested that, by inoculating each bacterial wilt disease strain infected with a φRSM-type filamentous phage to an appropriate crop or garden plant, infection with a wilt bacterium can be prevented for a long period (at least 2 months).

Further, the present inventors also discovered that an RSM phage prepared by replacing the host recognition protein of the φRSM1 phage with the φRSM3 phage type by recombination shows the same host specificity as the host specificity of the φRSM3 phage. That is, it is suggested that, also by using as an effective component a wilt bacterium infected with an RSM phage having the φRSM1 phage-type host recognition protein and/or an RSM phage having the φRSM3 phage-type host recognition protein, an agent for preventing bacterial wilt disease for each appropriate crop or garden plant can be obtained. For details of the host recognition proteins of the φRSM1 phage and the φRSM3 phage, see Non Patent Literature 3.

The present invention is not limited by the descriptions in the modes and Examples of the present invention. Various modified modes are also included in the present invention within the scope of the description of the Claims as long as those skilled in the art can easily infer the modes.

The entire contents of the papers and Japanese Laid-open Patent Applications clearly specified in the present description are hereby incorporated by reference.

The present application is based on Japanese Patent Application No. 2011-102153, filed on Apr. 28, 2011. The entire description, Claims and drawings in Japanese Patent Application No. 2011-102153 are hereby incorporated by reference into the present description.

INDUSTRIAL APPLICABILITY

The present inventors discovered that a wilt bacterium infected with the ϕRSM1 phage or the ϕRSM3 phage loses the pathogenicity and does not develop bacterial wilt disease even after inoculation of the bacterium to a plant such as tomato. The present inventors also discovered that, by preliminarily inoculating a wilt bacterium infected with such a phage to a plant such as tomato, the plant shows strong resistance to inoculation of a wilt bacterium thereafter, and does not develop bacterial wilt disease for at least two months. Further, the present inventors discovered that, since the ϕRSM1 phage and the ϕRSM3 phage have largely different host specificities from each other, use of the two phages allows utilization of a total of 15 bacterial strains of different races, biovars and phylotypes as preventive vaccines for bacterial wilt disease. Thus, it is expected that most naturally occurring bacterial wilt disease strains can be infected with the above two phages.

Thus, the present invention provides: an agent for preventing bacterial wilt disease, which agent can prevent the development of bacterial wilt disease caused by various different bacterial wilt disease strains, that is, the development of bacterial wilt disease in various different plant varieties; and a method for preventing bacterial wilt disease utilizing the agent for preventing bacterial wilt disease. More specifically, by treating seedlings (at the stage of cultivation in a pot, before transplantation to a field, flower bed or the like) of major crops such as tomato, potato, green pepper, eggplant and tobacco, and garden plants by the technique of the present invention, development of bacterial wilt disease after the transplantation can be remarkably prevented. Such results lead to prevention of the damage by bacterial wilt disease, which is estimated to be causing loss of about 9.5 trillion yens per year in the world, and to avoidance of problems such as complex environmental pollution and pesticide residues by use of chemical pesticides.

The invention claimed is:

1. A method for preventing bacterial wilt disease, comprising inoculating with an agent for preventing bacterial wilt disease comprising as an effective component a wilt bacterium (*Ralstonia solanacearum*) infected with a φRSM1 filamentous phage and a wilt bacterium (*Ralstonia solanacearum*) infected with a ϕRSM3 filamentous phage into a plant that needs prevention of bacterial wilt disease caused by wilt disease bacterium having pathogenicity, thereby preventing bacterial wilt disease in plants later exposed to a pathogenic wilt disease bacterium for at least two months.

2. The method for preventing bacterial wilt disease according to claim 1, wherein the plant is any one of tomato, potato, green pepper, eggplant, tobacco, capsicum, Japanese basil, Japanese radish, strawberry, banana, marguerite, chrysanthemum and sunflower.

3. The method for preventing bacterial wilt disease according to claim 2, wherein the plant is any one of tomato, potato, green pepper, eggplant and tobacco.

4. The method for preventing bacterial wilt disease according to claim 1, wherein the method for preventing bacterial wilt disease comprises inoculating a plant with a wilt bacterium (*Ralstonia solanacearum*) infected with the ϕRSM1 filamentous phage and a wilt bacterium (*Ralstonia solanacearum*) infected with the ϕRSM3 filamentous phage in an amount of $10^5$ to $10^8$ cells/g plant body weight.

5. The method for preventing bacterial wilt disease according to claim 4, wherein the method for preventing bacterial wilt disease comprises inoculating a plant with a wilt bacterium (*Ralstonia solanacearum*) infected with the ϕRSM1 filamentous phage and a wilt bacterium (*Ralstonia solanacearum*) infected with the ϕRSM3 filamentous phage in an amount of $10^6$ to $10^7$ cells/g plant body weight.

6. The method for preventing bacterial wilt disease according to claim 1, wherein the agent for preventing bacterial wilt disease is inoculated into the stem of the plant.

7. The method for preventing bacterial wilt disease according to claim 6, wherein the agent for preventing bacterial wilt disease is inoculated into the stem of the plant at a site 1 to 4 cm distant from the soil.

8. The method for preventing bacterial wilt disease according to claim 1, wherein the agent for preventing bacterial wilt disease is inoculated 2 to 4 weeks after germination of the plant.

9. The method for preventing bacterial wilt disease according to claim 1, wherein the wilt bacterium (*Ralstonia solanacearum*) strain infected with the ϕRSM1 filamentous phage is any one of M4S, Ps29, Ps65 and Ps74.

10. The method for preventing bacterial wilt disease according to claim 1, wherein the wilt bacterium (*Ralstonia solanacearum*) strain infected with the ϕRSM3 filamentous phage is any one of C319, Ps72 and Ps74.

* * * * *